United States Patent [19]

Wilcox

[11] Patent Number: 5,169,760

[45] Date of Patent: Dec. 8, 1992

[54] METHOD, VECTORS, AND HOST CELLS FOR THE CONTROL OF EXPRESSION OF HETEROLOGOUS GENES FROM LAC OPERATED PROMOTERS

[75] Inventor: Edward R. Wilcox, Escondido, Calif.

[73] Assignee: Mycogen Corporation, San Diego, Calif.

[21] Appl. No.: 386,821

[22] Filed: Jul. 27, 1989

[51] Int. Cl.⁵ .................... C12N 15/11; C12N 15/67
[52] U.S. Cl. ........................... 435/69.1; 435/252.3; 435/320.1; 536/27
[58] Field of Search ............. 435/69.1, 172.3, 39, 435/252.3, 320.1; 536/27

[56] References Cited

PUBLICATIONS

Gene, 51:255–267, 1987, Stark, Multicopy Expression Vectors Carrying the lac Repressor Gene for Regulated High-Level Expression of Genes in *Escherichia coli*.

Beckwith, J., (1987), "The Lactose Operon", in *Escherichia coli* and *Salmonella typhimurium* Cellular and Molecular Biology, vol. 2, Neidhardt, F. C., Editor in Chief, American Society for Microbiology, Washington, D.C.

Freifelder, D., (1987), "*Molecular Biology*", Jones and Bartlett Publishers, Inc., Portola Valley, Calif.

Jobe, A., Bourgeois, S., (1972), "The Natural Inducer of the lac Operon", J. Mol. Biol., 69:397–408.

Muller-Hill, H. V. Rickenberger and K. Wallenfels, (1964), "Specifiecity of the Induction of the Enzymes of the lad Operon in *Escherichia coli*", J. Mol. Biol., 10:303–318.

*Primary Examiner*—David L. Lacey
*Assistant Examiner*—John D. Ulm
*Attorney, Agent, or Firm*—Saliwanchik & Saliwanchik

[57] ABSTRACT

The invention is a process for controlling the expression of heterologous genes from lac-operated promoters by removing the CAP binding site and lac promoter from the lac operon. Illustrated is the fusion of the lacZ, Y, and A genes of the lac operon to the 3' end of the lacI structural gene. This elimination of the natural regulatory elements of the lac operon results, advantageously, in the production of lac operon gene products in a constitutive mode from the lacI promoter.

16 Claims, 9 Drawing Sheets

METHOD, VECTORS, AND HOST CELLS FOR THE CONTROL OF EXPRESSION OF HETEROLOGOUS GENES FROM LAC OPERATED PROMOTERS

BACKGROUND OF THE INVENTION

The lactose (lac) operon consists of three protein products under the control of a lac promoter-operator. These gene products are β-galactosidase (Z), permease (Y), and thiogalactoside transacetylase (A). The protein product of the lacI transcript (repressor), an independent gene product, interacts with the operator of the lac operon and keeps synthesis off until allolactose (1,6-0-β-D-galactopyranosyl-D-glucose), a product of the β-galatosidase reaction, accumulates in the cell and binds to the repressor. The allolactose repressor complex has a changed conformation, allowing the repressor to be displaced from the operator. RNA transcription then begins from the lac promoter (Beckwith, J. [1987] In *Escherichia coli and Salmonella typhimurium Cellular and Molecular Biology*. Vol. 2, Neidhardt, F. C., Editor in Chief, American Society for Microbiology, Washington, D.C.).

A few molecules of the lac operon transcript are present in *E. coli*, even in the absence of lactose. Hence, permease and β-galactosidase are always present, at least at a low level. Allolactose, the natural inducer of the operon, is made in the cell when lactose (1,4-0-β-D-galactopyanosyl-D-glucose) enters the cell by the permease reaction and is converted through transgalactosidation by β-galactosidase into allolactose (Freifelder, D., [1987] *Molecular Biology*. Jones and Bartlett Publishers, Inc., Portola Valley, CA; Beckwith, supra). It was calculated that greater than 20% of the lactose acted upon by β-galactosidase is converted to allolactose (Jobe, A., Bourgeois, S., [1972] J. Mol. Biol. 69:397–408). The majority of the remaining lactose is converted to glucose and galactose. Allolactose is a better substrate for β-galactosidase than lactose (Jobe and Bourgeois, supra), and is itself rapidly converted to glucose and galactose.

Another control element of the lac operon is catabolite repression. In the presence of glucose the cell is able to repress many operons. For example the lac operon is only transcribed at 2% of its maximum level in the presence of glucose (Beckwith, supra).

When several β-galactosides were compared for their ability to induce the lac operon in vivo, lactose was found to act as a very poor effector molecule. The synthetic non-metabolized β-galactoside, isopropyl-β-D-thiogalactoside (IPTG), was found to induce the lactose operon 5 times better than lactose (Monod, J., G. Cohen-Bazire and M. Cohn [1951] Biochim. Biophys. Acta. 7:585–599). Yet, allolactose itself is as good an inducer of the operon as IPTG (Muller-Hill, B., H. V. Rickenberg and K. Wallenfels [1964] J. Mol. Biol. 10:303–318; Jobe and Bourgeois, supra).

Given the efficiency of lactose conversion to allolactose, one might expect lactose to work very well as an inducer of the lac operon. However, prior to the present disclosure, this has never occurred in practice (Monod et al., supra).

The current way to control the expression of heterologous genes from the lac promoter or lac concensus promoters such as tac (Rezinkoff, W. S. and W. R. McClure [1986] *Maximizing Gene Expression*, W. Reznikoff and L. Gold, eds., Butterworth Publishers, Stoneham, MA) is to have enough lac repressor present in the cell, so that transcription from the tac promotor is off until IPTG or another proper inducing β-galactoside is added to the cell. Although IPTG is the current inducer of choice, it is expensive and has been labeled a potential carcinogen. Thus, there is a need to replace IPTG in commercial systems where control of the expression of heterologous genes from lac operated promoters is used.

BRIEF SUMMARY OF THE INVENTION

The subject invention concerns an improved method for controlling the expression of heterologous genes from lac operated promoters. Specifically, the subject invention concerns a method for controlling the expression of heterologous genes from lac operated promoters which comprises removing the CAP binding site and lac promoter/operator from the lac operon. The subject invention is exemplified herein by use of a novel recombinant DNA construct comprising the lacZ, Y, and A genes of the lac operon, to control the expression of heterologous genes from lac operated promoters. The lacZ, Y, and A genes of the lac operon were fused to the 3' end of the lacI structural gene, thereby eliminating all of the natural regulatory elements of the lac operon. By doing this, lac operon gene products are produced in a constitutive mode from the lacI promoter and are not responsive to catabolite repression or to allolactose induction. When lactose is added, the constitutively synthesized β-galactosidase converts as much as 20% to allolactose, which in turn derepresses the tac promoter and any associated heterologous gene. As long as the allolactose concentration in the cell is above $10^{-5}$M, the tac promoter provides high expression of the protein of interest. The complete DNA sequence of the transcriptional fusion of the lacI gene to the lacZ, Y, and A genes of the subject invention is as shown in Table 1.

The novel lacIZYA operon (Table 1) can be inserted in any plasmid, or it can be inserted into any microbial chromosome to improve control of heterologous gene expression from a lac operated promoter (as long as a promoter is present to drive lacIZYA transcription). It will be apparent to a person skilled in the art that other constructs can be used to fuse the genes.

The lac operator, which has very high affinity for the lacI repressor ($K_{DNA}=2-5\times10^{13}$ $M^{-1}$), is a sequence 21 b.p. long as follows; AATTGTGAGC-GGATAACAATT (Barkley, M. D. and S. Bourgeois [1978] In *The Operon* Miller, J. H. and W. S. Reznikoff, eds. Cold Spring Harbor). Many mutations within the lac operator exist which have higher or lower affinities to the lacI repressor (Barkley and Bourgeois, supra; Sadler, J. R. et al. [1983] Proc. Natl. Acad. Sci. USA 80:6785–6789; Simons, A. et al. [1984] Proc. Natl. Acad. Sci. USA 81:1624–1628). Many mutations exist within the lacI repressor that allow for greater affinity to the lac operator with no significant effect on derepression (Barkley and Bourgeois, supra). Using any of the many different combinations of lac operator and lacI repressor, the control of heterologous gene expression is apparent to a person skilled in the art. Many different promoters (eukaryotic as well as prokaryotic) have been placed under lac operator regulation (Yansura, D. G. and D. J. Henner [1984] Proc. Natl. Acad. Sci. USA 81:439–443; Herrin Jr., G. L. and G. N. Bennett [1984] Gene 32:349–356; Deuschle, U., et al. [1986] Proc. Natl.

Acad. Sci. USA 83:4134–4137; Hu, M. C-T. and N. Davidson [1988] Gene 62:301–314; Figge, J., et al. [1988] Cell 52:713–722). The subject invention is designed to improve lactose induction from such lac operated promoters.

This invention enables cells to make enough lacZ and Y protein to efficiently take up lactose and convert it to glucose and galactose, as well as to the true lac inducer, allolactose. In addition, the invention enables the cell to synthesize enough repressor (lacI protein) to bind to the lac operator upstream from a heterologous gene, and keep heterologous gene expression off in the absence of inducer. With excess lactose present in the medium, the cell can accumulate sufficient concentrations of allolactose for efficient derepression of the lac operator.

A synthetic fragment of DNA was cloned into pUC18 to replace the normal sequence found at Hind III-403 to HaeII-524. This synthetic sequence removes the lac promoter and operator sequences and replaces them with a Shine-Dalgarno site.

FIGS. 2*a* to *d*-pMYC 2101, construction of the lacI-ZYA operon

Three fragments of DNA were ligated and then introduced by transformation into MC1061 (Casadaban, M. and S. Cohen [1980] J. Mol. Biol. 138:179–207) to construct the plasmid pMYC2101. The first fragment came from pMYC2005 as a HindIII-403 to EaeI-485 piece, the second fragment came from pMC9 as an EcoRI-1 to EaeI-1103 piece and the final fragment comes from pSKS107 as a 9889 bp HindIII-31 to EcoRI-1 piece. Once constructed, the EcoRI and SalI ends were converted to BamHI and BglII ends, respectively, using oligonucleotide linkers, creating pMYC2101-B.

Figure 3:
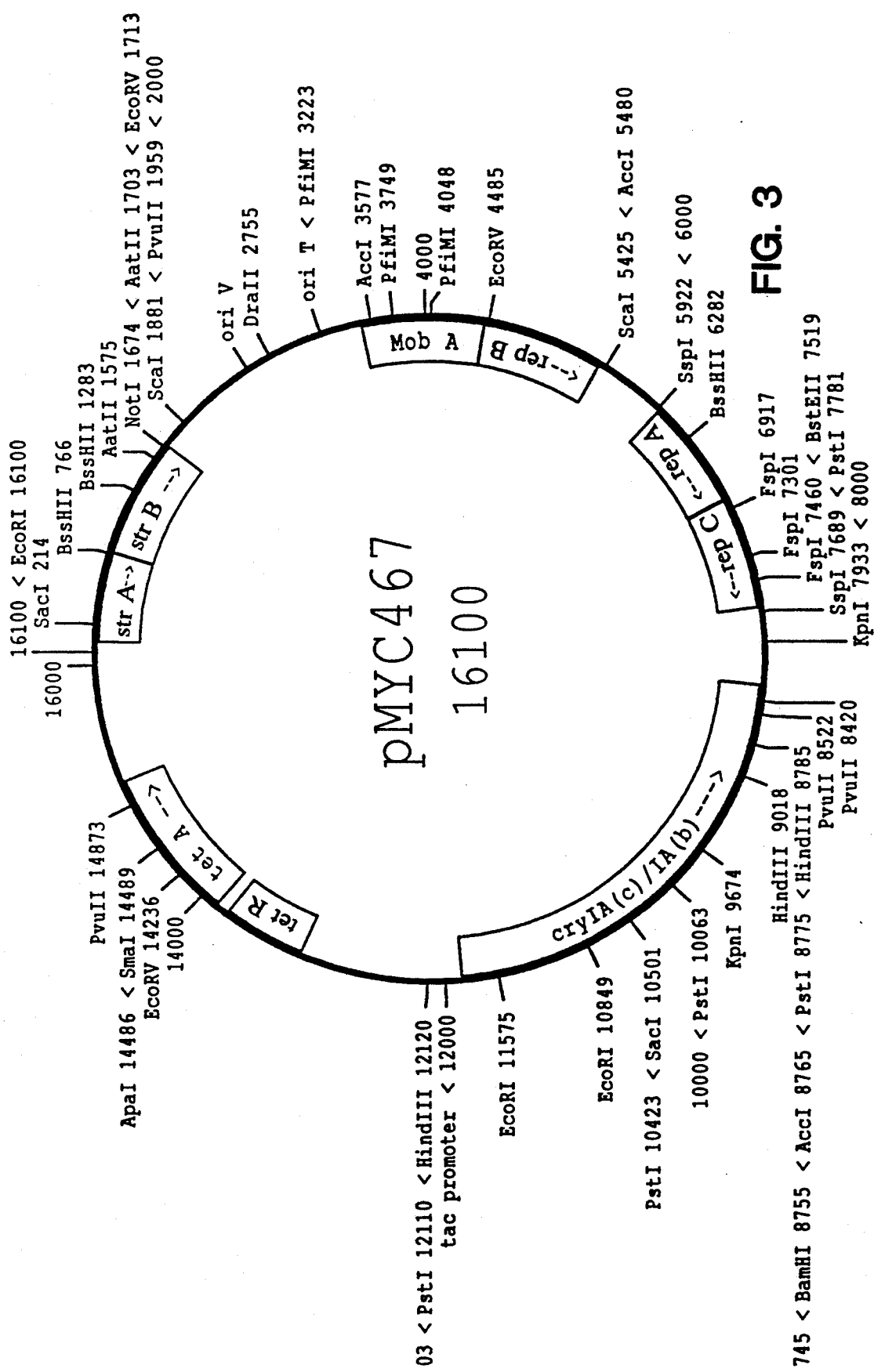

FIG. 3 -pMYC467, a tac promoted toxin-containing plasmid

The tac promoted toxin gene found in pMYC436 (NRRL deposit no. B-18292) was cloned as a 4.5 Kbp BamHI to PstI fragment in the vector pTJS260. Not all the sequence of pTJS260 or of the 3′ flanking sequences of the toxin genes are available, hence some restriction sites are approximated in FIGS. 3, 4, 5 and 6.

Figure 4:
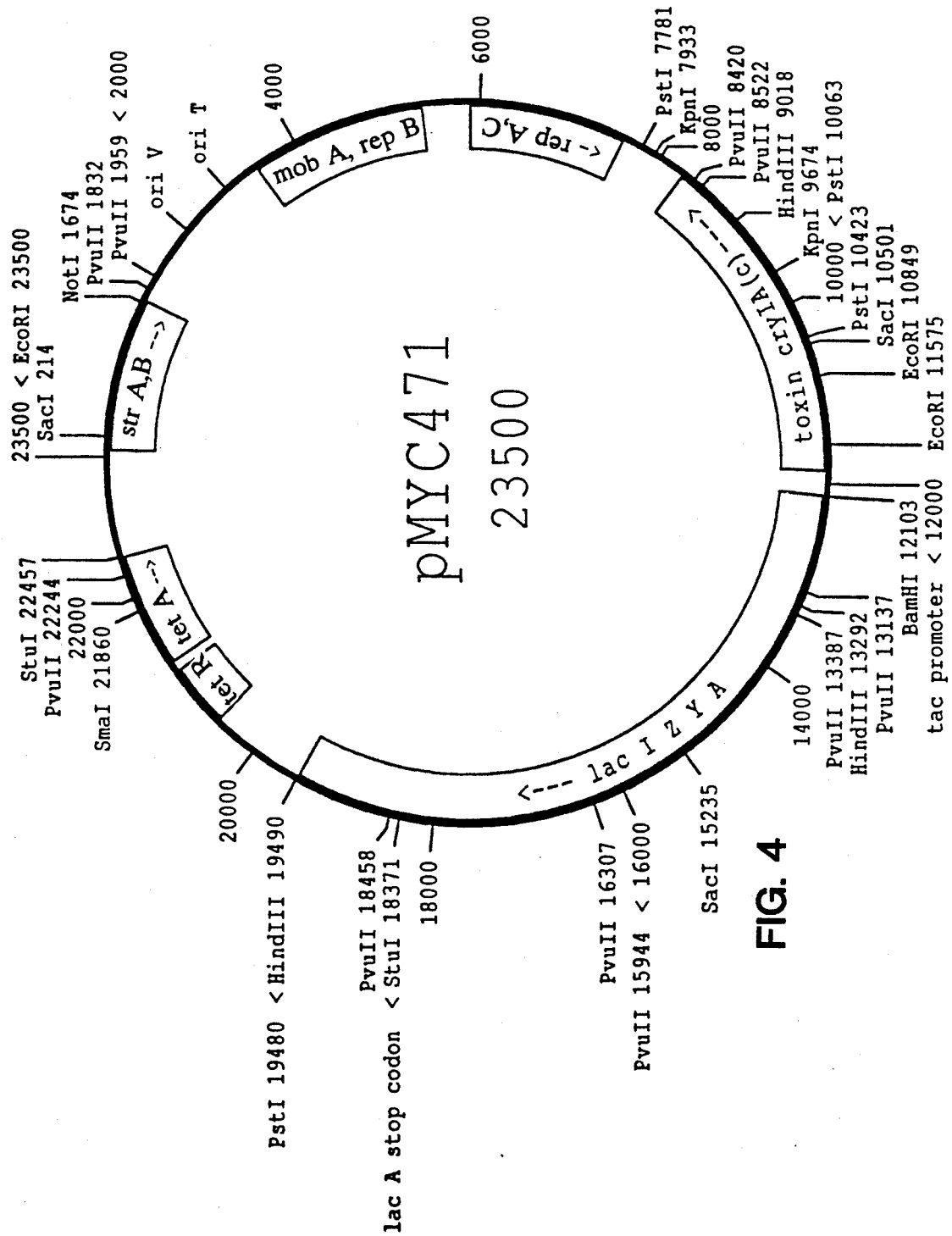

FIG. 4 -pMYC471, a lactose inducible plasmid

The lacIZYA operon was cloned into the BamHI site of pMYC467. The resulting plasmid, pMYC471, was then induced by transformation into MB101, a *P. fluorescens.*

Figure 5:
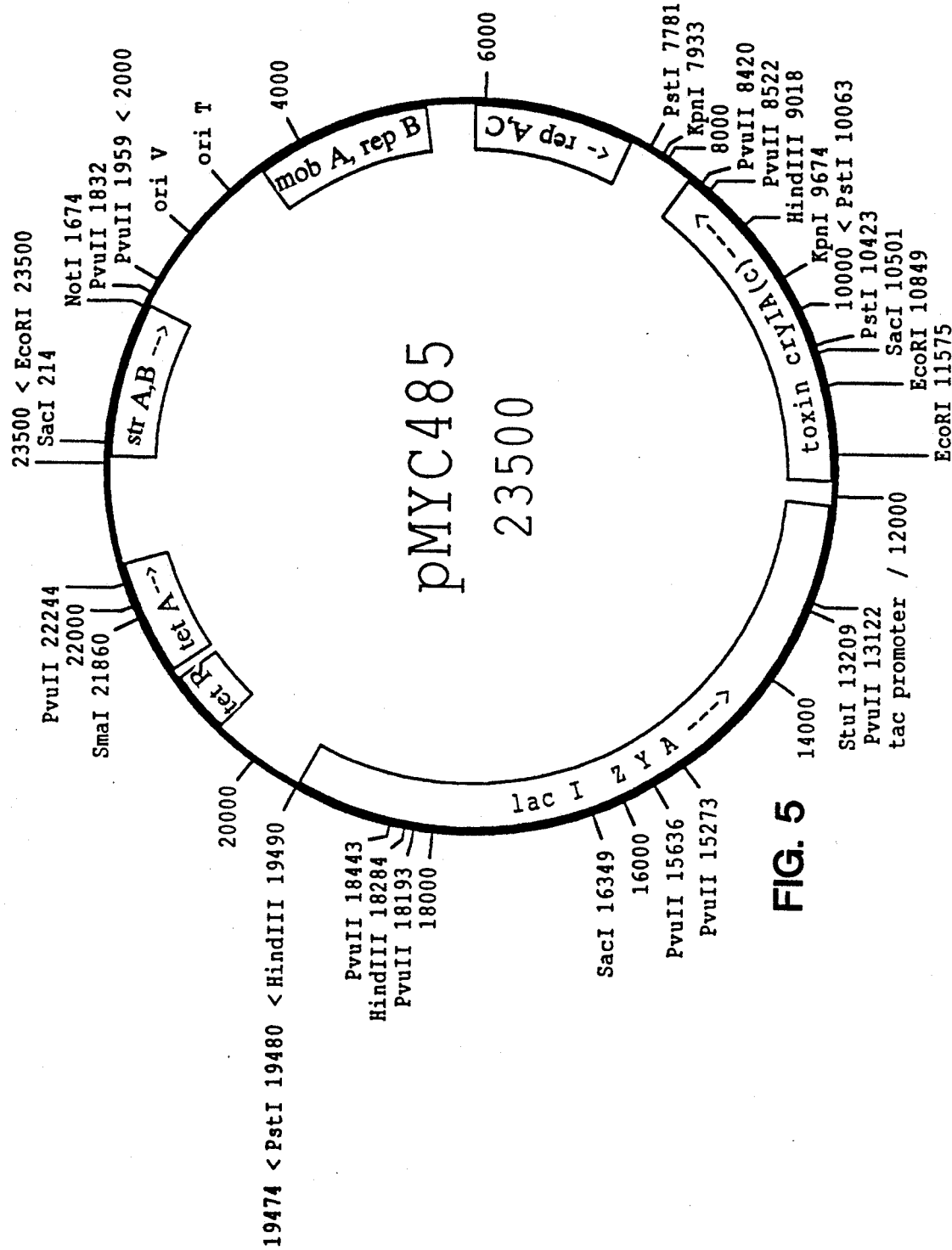

FIG. 5-pMYC485, an alternate lactose inducible plasmid

A lacI$^Q$ ZYA operon was constructed by replacing lacI with lacI$^Q$ as a 638 bp BamHI to ApaI fragment. The lacI$^Q$ZYA operon was then cloned into the BamHI site of pMYC467. The resulting plasmid, pMYC485, was tested in MB101 for lactose inducibility. The lacI$^Q$ ZYA operon is shown in Table 1 wherein base 16 is a T instead of a C as shown in the table.

Figure 6:
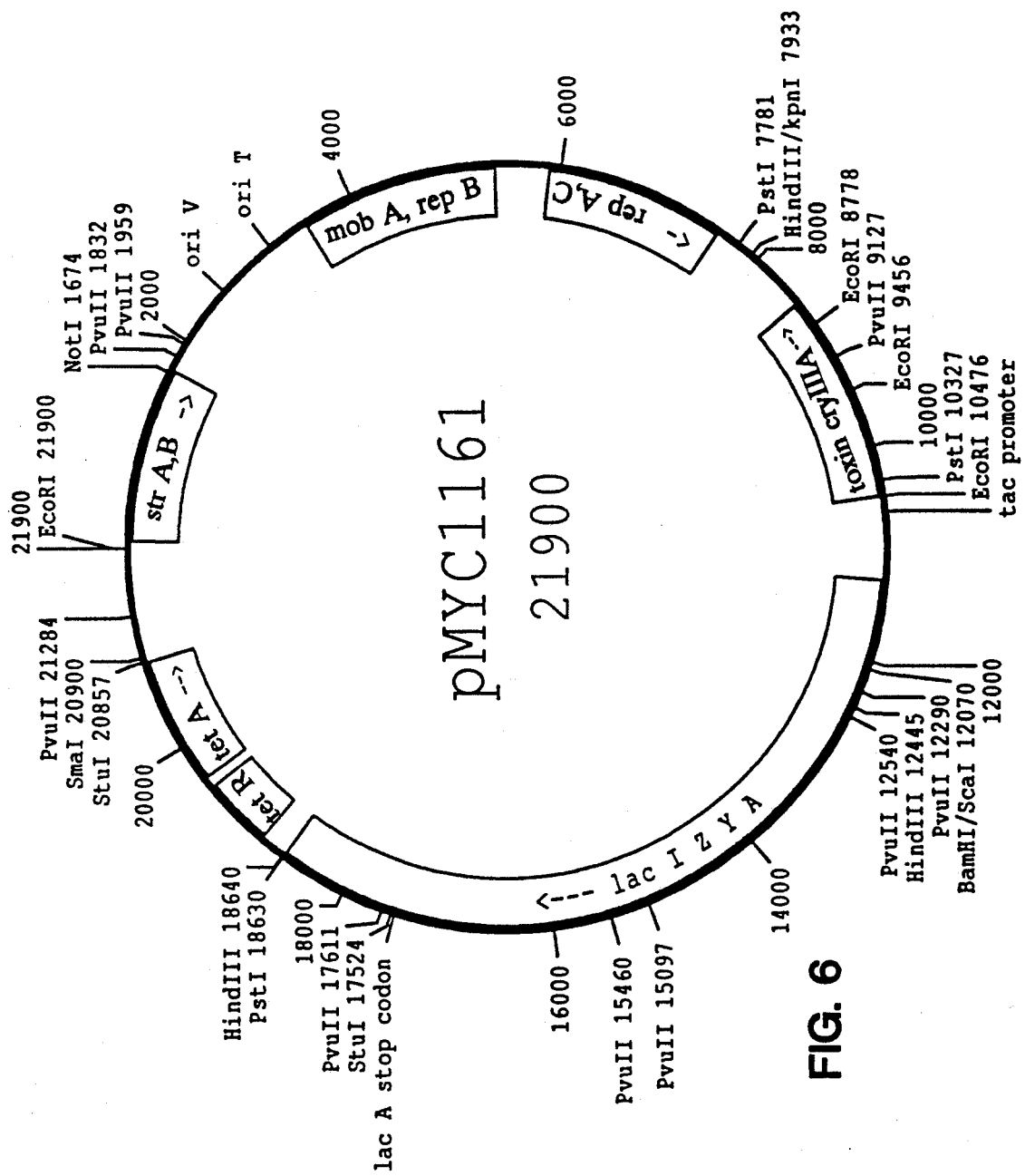

FIG. 6-pMYC1161, a coleopteran toxin-lactose inducible plasmid

The plasmid pMYC471 was cut with BamHI (at position 12103) and KpnI (at position 7933) to remove the tac-promoted lepidopteran-active toxin and then both ends were filled in with T4 DNA polymerase, resulting in blunt termini. The tac promoted toxin gene disclosed in U.S. Pat. No. 4,771,131, was inserted into the above DNA as a blunt-ended ScaI (of pBR322) to filled-in HindIII fragment (at the 3′ end of the coleopteran-active sequence). The 5′ end of the tac promoter had been previously inserted by blunt-end ligation into the EcoRI site of pBR322.

DETAILED DISCLOSURE OF THE INVENTION

Upon removal of the CAP binding site and lac promoter/operator from the lac operon, there is realized an improved control of expression of a heterologous gene. Exemplified herein is the insertion of a lacI-ZYA fusion construct into a plasmid containing a tac-promoted gene encoding a lepidopteran insect toxin. The plasmid (pMYC471) was then used to transform *Pseudomonas fluorescens*, which was designated *Pseudomonas fluorescens* MR471 (pMYC471).

One element of plasmid pMYC471 provides its host with constitutive levels of lac operon gene products. For this purpose, the operon could be fused to any of a variety of available constitutive promoters. In this instance, it was fused to the lacI promoter. In addition, a new construct containing a lacI$^Q$ promoter, instead of the lacI promoter, was made (pMYC485). This new construct provides higher levels of the repressor as well as of lac operon gene products. The plasmid, pMYC485, functions like pMYC471.

As a demonstration that lactose inducibility is not dependent on the specific gene under tac promoter control, another gene encoding a coleopteran-active toxin was cloned into the pMYC471 vector replacing the lepidopteran-active toxin gene, resulting in pMYC1161. *Pseudomonas fluorescens* strain MB101 carrying this new plasmid also permits lactose induction of toxin expression. This will hold true for any gene under control of a lac operated promoter.

Another aspect of this fusion is that the lac operon is no longer regulated by the normal control elements associated with lactose. This means that synthesis of lac operon ZYA gene products in these constructs (pMYC471, pMYC485, and pMYC1161) is constitutive and occurs independently of the concentrations of lactose or glucose present in the cell. For example, in the presence or absence of IPTG or lactose, a new protein band corresponding to the mass of β-galactosidase is apparent on SDS-PAGE and the clones cleave X-gal, forming blue colonies under the same conditions.

For ease in construction, the lacA gene has been included on all the plasmids contining lacIZYA mentioned in this disclosure. The lacA gene product has no role (Freifelder, supra) in production of allolactose and can easily be removed from the lacIZYA operon. For example, there is a nonunique AflII (CTTAAG) restriction enzyme site a the stop codon of the lacY gene. By using this AflII restriction site, it is possible to remove the lacA gene. The lacIZY operon has the same lactose induction properties as those found in the lacIZYA operon.

The data of Table 2 demonstrate toxin production is regulated by lactose or IPTG. Although the amount of lactose used for induction is 10 to 20 fold higher than IPTG induction levels, the significantly reduced cost of lactose ($7.00 per kilo, Sigma Chemical Co.) compared to IPTG ($20,000 per kilo, Sigma Chemical Co.) make the former inducer highly economically advantageous. For maximum production levels the metabolized substrate, lactose, must be replenished during cell growth or the culture will decrease the synthesis of the tac-promoted gene.

Materials and Methods

Cloning and DNA manipulation techniques are described in Maniatis, T., E. F. Fritsch and J. Sambrook (1982) *Molecular Cloning, a Laboratory Manual.* Cold Spring Harbor Laboratory Publishers, Cold Spring Harbor, N.Y.

380A oligonucleotide synthesizer. This sequence starts at BP 1073 of the lacI sequence (Farabaugh, P. J., supra) as seen in Table 1.

| Hae II | | | | | | | | | | | | Eae 1 |
|---|---|---|---|---|---|---|---|---|---|---|---|---|
| CC | AAT | ACG | CAA | ACC | GCC | TCT | CCC | CGC | GCG | TTG | GCC | GAT |
| CGCGGG | TTA | TGC | GTT | TGG | CGG | AGA | GGG | GCG | CGC | AAC | CGG | CTA |

| | | | | | | | Xho I | | | | | |
|---|---|---|---|---|---|---|---|---|---|---|---|---|
| TCA | TTA | ATG | CAA | CTC | GCA | CGA | CAG | GTC | TCG | AGA | CTG | GAA | AGC |
| AGT | AAT | TAC | GTT | GAG | CGT | GCT | GTC | CAG | AGC | TCT | GAC | CTT | TCG |

| lacI | | | | lacZ | | Hind III |
|---|---|---|---|---|---|---|
| Stop | | S/D | | Start | | |

| GGG | CAG | TGA | GCGCTAGGAGGTAACTT | ATG | GAA |
|---|---|---|---|---|---|
| CCC | GTC | ACT | CGCGATCCTCCATTGAA | TAC | CTTTCGA |

A plasmid containing the lac operon, pSKS107, was received from Dr. M. Casadaban at the University of Chicago (Shapira, S. K., J. Chou, F. V. Richaud and M. J. Casadaban [1983] Gene 25:71-82). The sequence of the lac operon is published (Kalnins, A., K. Otto, U. Ruther and B. Muller-Hill [1983] EMBO J. 2:593-597; Hediger, M. A., D. F. Johnson, D. P. Nierlich and I. Zabin [1985] Pro. Nat. Acad. Sci. 82:6414-6418). The lacI gene, on a 1.7 KB EcoRI restriction fragment cloned into pBR322, is available from the ATCC, as pMC9, catalogue no. 37195, 37196 and 37197. The sequence of the lacI gene is also published (Farabaugh, P. J. [1978] Nature 274:765-769). The broad host range vector, pMMB22, was received from Dr. M. Bagdasarian (Bagdasarian, M. M., E. Amann, R. Lurz, B. Ruckert and M. Bagdasarian [1983] Gene 26:273-282). A HindIII fragment of pMMB22, containing the lacI$^Q$ gene, was relinkered to BamHI. The sequence of the lacI$^Q$ gene has also been published (Calos, M. P. [1978] Nature 274:762-765). Analysis here is largely based on the published DNA sequences. Some of the critical portions of the constructs were confirmed by DNA sequencing, e.g., the lacI and lacI$^Q$ promoters and the fusion region between the lacI transcriptional unit and the lac operon. The vector, pUC18, is available from a variety of sources, such as catalogue no. 27-4949-01 of Pharmacia Corporation. The broad host range vector, pTJS260, is available from Dr. D. R. Helinski at the University of California, San Diego, La Jolla CA. 92093 (Schmidhauser, T. J. [1986] Ph.D Thesis, UCSD).

Following are examples which illustrate procedures, including the best mode, for practicing the invention. These examples should not be construed as limiting. All percentages are by weight and all solvent mixture proportions are by volume unless otherwise noted.

EXAMPLE 1

Fusions of the LacI Gene and Lac Operon.

Figure 1:
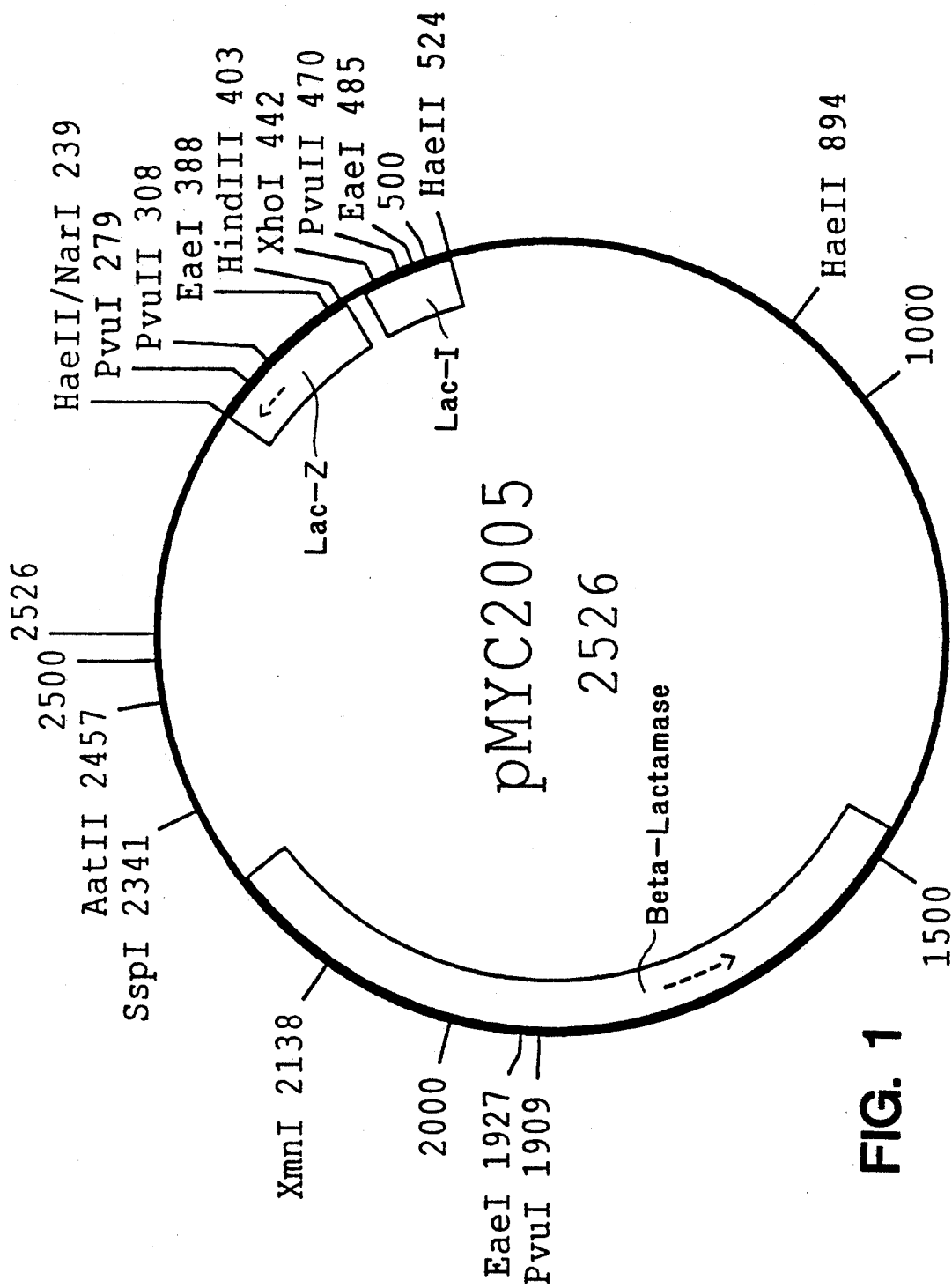
FIG. 1-pMYC 2005, LacI and Z operon fusion
Figure 2A:
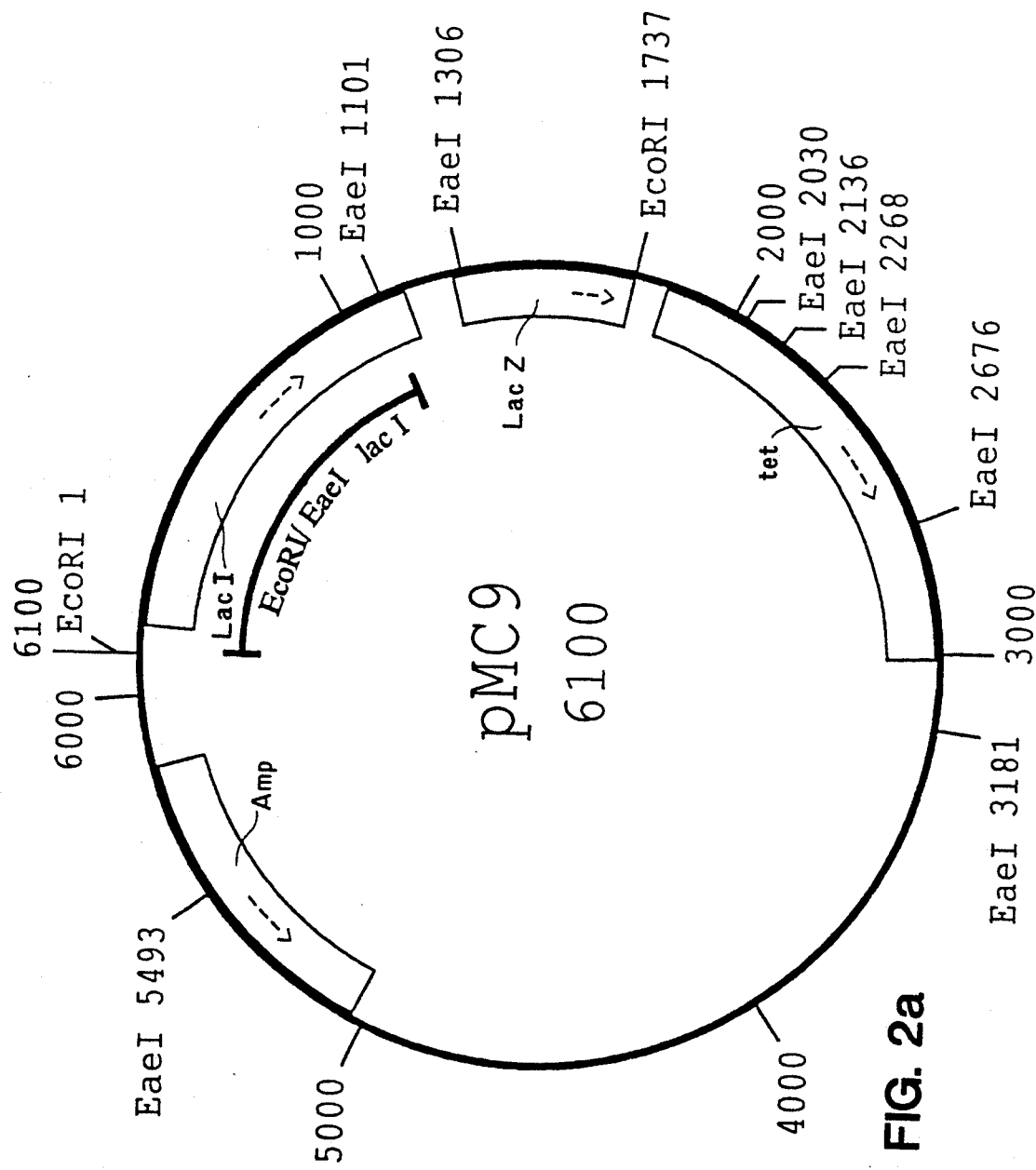
Figure 2B:
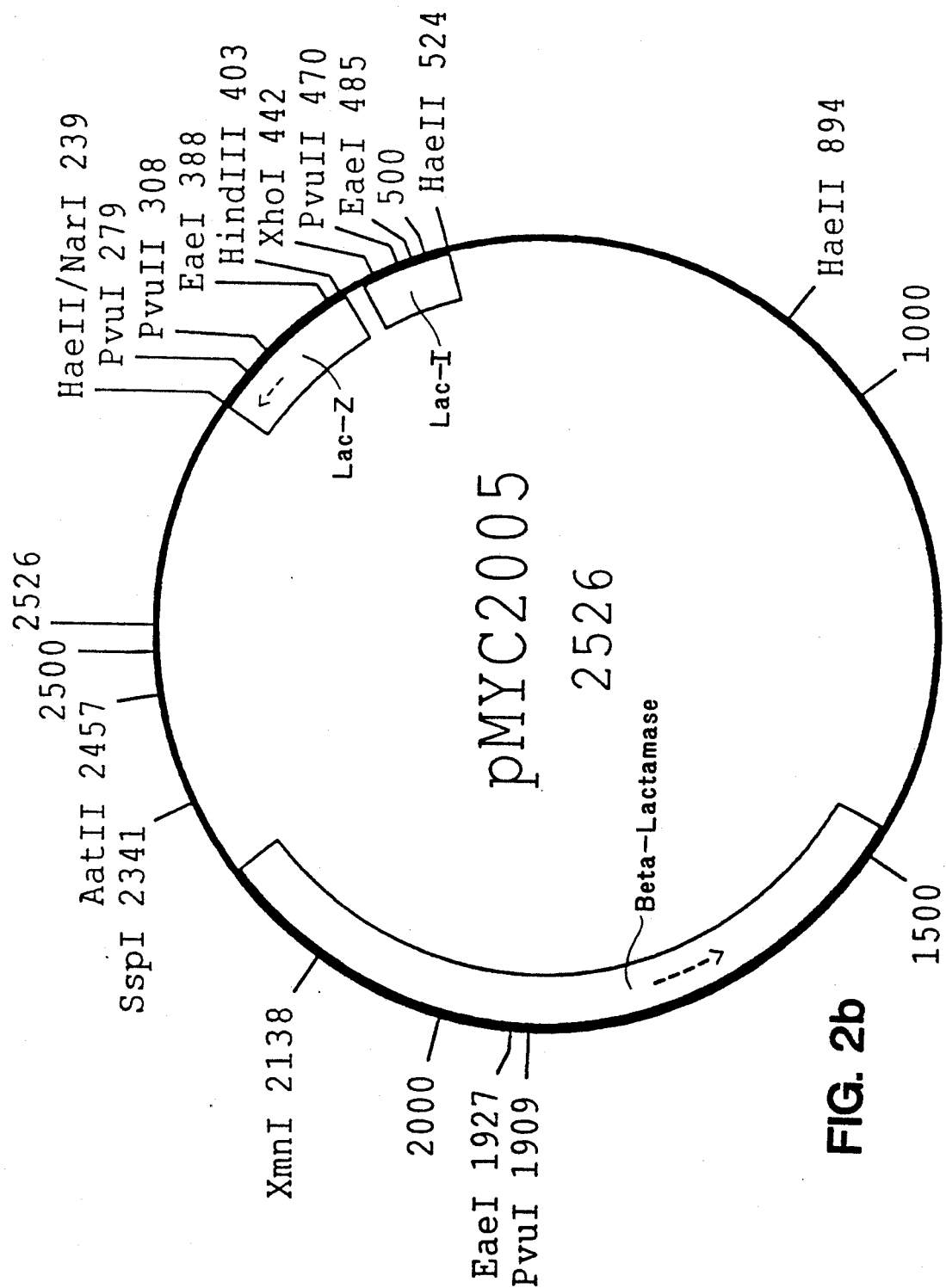
Figure 2C:
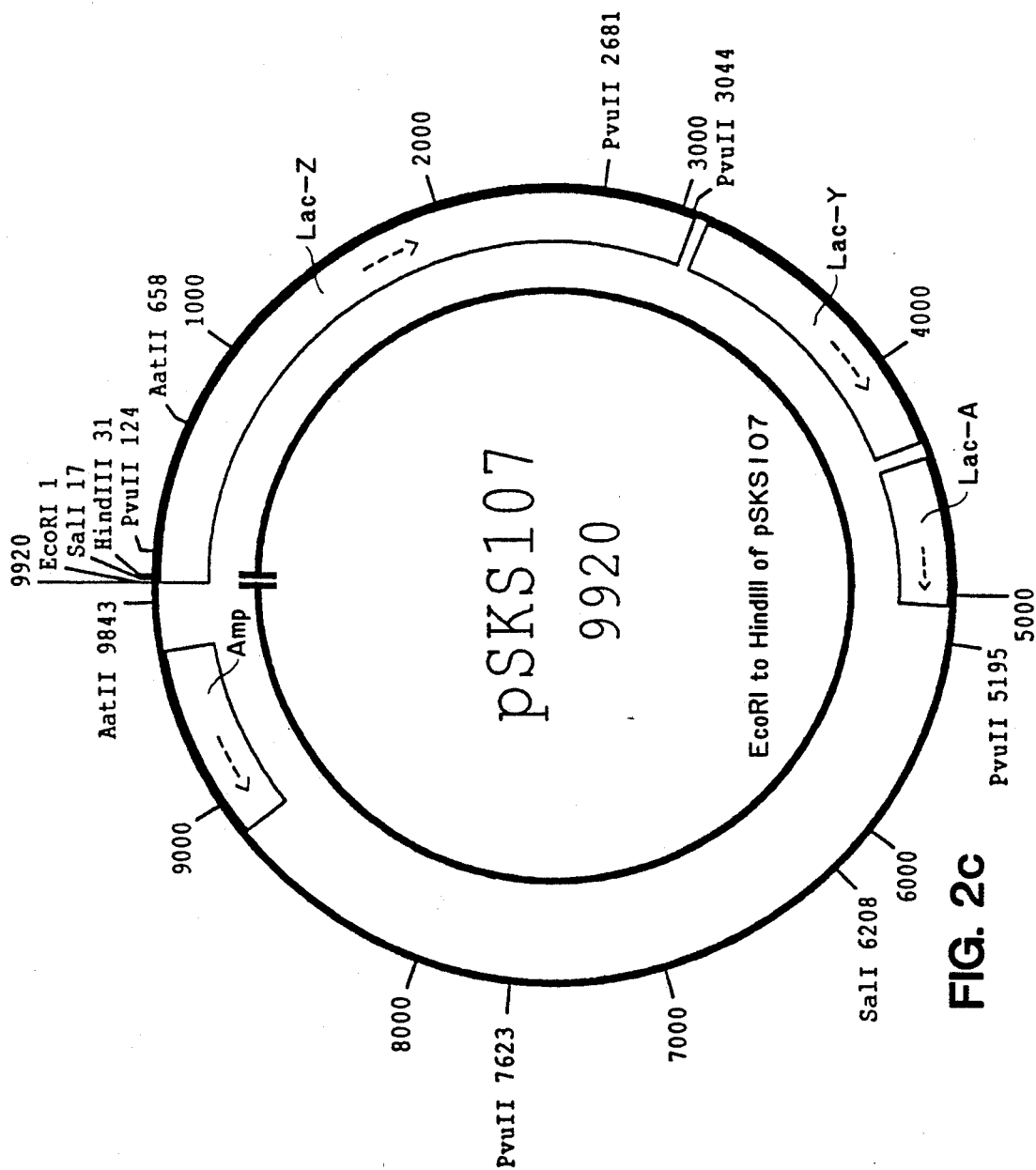
Figure 2D:
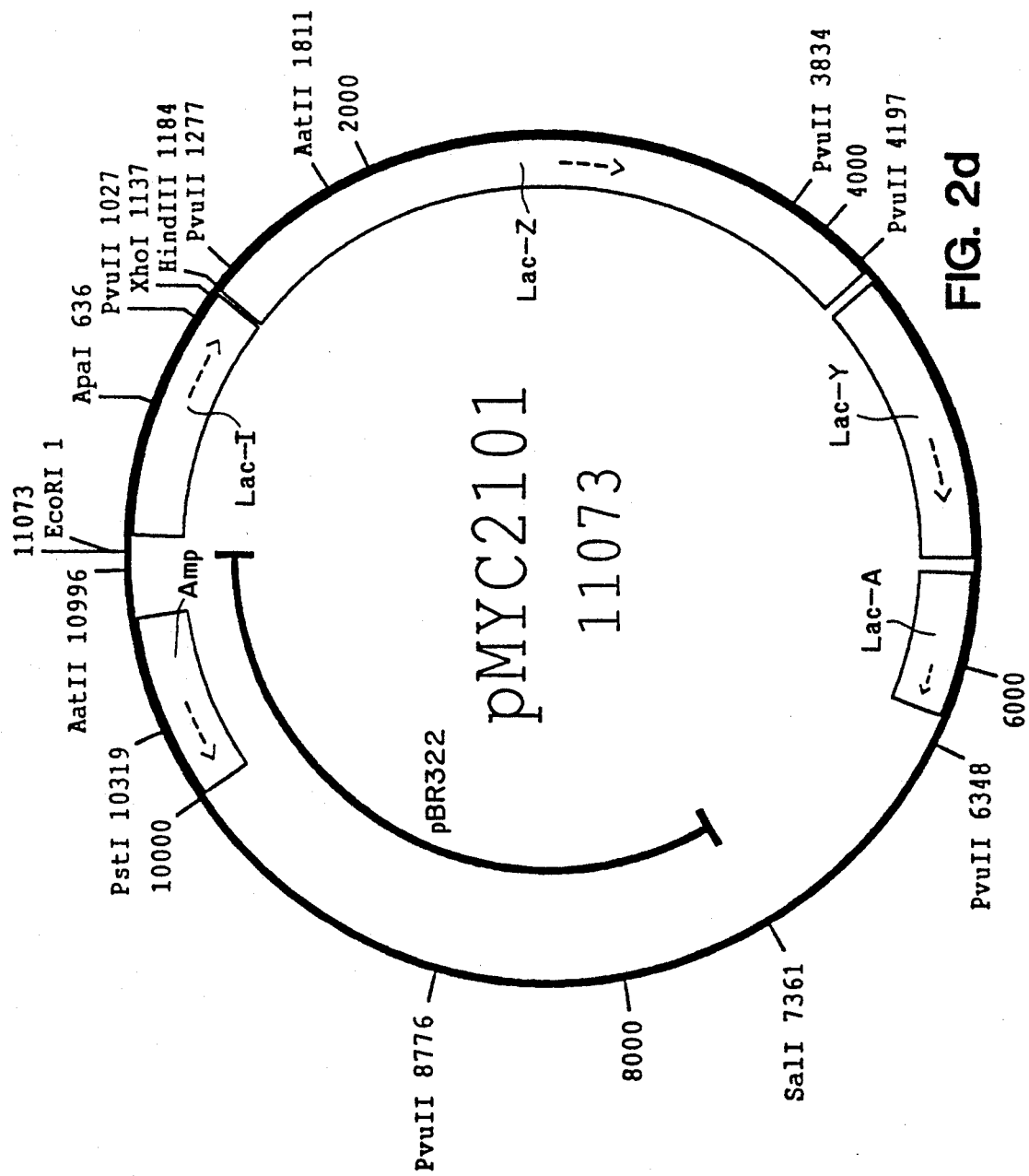

Fusions of the lacI gene and lac operon were first carried out in pUC18. To do so, pUC18 was linearized with HindIII and then partially cut with HaeII. The DNA was resolved by electrophoresis on a 1.4% agarose gel. The 2402 bp band was eluted and ligated to a double-stranded synthetic DNA insert produced by β-cyanoester chemistry on an Applied Biosystems The above synthetic sequence removes the PvuII site normally found at BP 1123 of lacI. A new XhoI site was inserted near the 3' end of the lacI gene (BP 1137). These changes were introduced for ease in identification of the new construct. No amino acid changes would occur as a result of the mutations introduced in making the base pair changes for the above two restriction sites. In this construct, the distance between the stop codon of lacI and the start codon of lacZ is 17 base pairs. This region contains a ribosome binding site (marked as S/D) such that a ribosome translating the lacI transcript will be able to continue synthesis of the lacZ gene product from the same transcript. A plasmid diagram of pMYC2005 is seen in FIG. 1.

EXAMPLE 2

Confirmation of Sequence.

The synthetic portion of pMYC2005 was sequenced to validate its structure and was used in a three-piece ligation to tie the full lacI gene of pMC9 to the lac operon found in pSKS107 (FIGS. 2a to d). After transformation, the lacI/Z fusion region was sequenced from a blue colony on an LB+X-gal (5-bromo-4-chloro-3-indolyl-β-D-galactosidase, a colorimetric substrate for the presence of β-galactosidase) plate. Those restriction sites that were examined yielded fragments of the predicted sized (FIGS. 2a to d). The lacI promoter region was also confirmed by sequence analysis.

EXAMPLE 3

Cloning

The EcoRI and SalI ends of the lacIZYA construct (FIGS. 2a to d) were respectively relinkered to yield BamHI and BglII restriction sites. The lacIZYA operon was cloned into the unique BamHI site of pMYC467 (FIG. 3) yielding pMYC471 (FIG. 4). The plasmid, pMYC467, contains the tac promoted lepidopteran toxin gene of pMYC436 (a cryIA(c)-like toxin gene [NRRL deposit no. B-18292] Adang, M. J. et. al. [1985] Gene 36:289-300) cloned into the broad host range vector, pTJS260. pMYC471 was introduced by transformation into *P. flourescens* MB101 and the resulting clone was designated MR471. MR471 was tested for the key elements of the resident pMYC471 plasmid. A functional repressor is synthesized because in the absence of IPTG or lactose no significant amount of toxin is produced (Table 1). The cells are blue when plated on X-gal because a functional β-galactosidase is present. A functional permease and β-galactosidase are present because the cells are able to induce the tac promoter in the presence of lactose (Table 1).

The subject invention can be used with any heterologous gene to control its expression from lac operated promoters. The expression product (protein) can be isolated from the culture medium of the producing microbe by means known in the art for isolating such a product from microbial cultures. Alternatively, a product which remains intracellular can be used in the form of the microbe itself, for example, as a biological insecticide. See U.S. Pat. Nos. 4,695,455 and 4,695,462 for such uses.

TABLE 1

|  |  | T in lac I$^Q$ |  |  |  |
|---|---|---|---|---|---|
| 1 | GACACCATCG | AATGGCGCAA | AACCTTTCGC | GGTATGGCAT | GATAGCGCCC |
|  |  | start codon lac I |  |  |  |
| 51 | GGAAGAGAGT | CAATTCAGGG | TGGTGAATGT | GAAACCAGTA | ACGTTATACG |
| 101 | ATGTCGCAGA | GTATGCCGGT | GTCTCTTATC | AGACCGTTTC | CCGCGTGGTG |
| 151 | AACCAGGCCA | GCCACGTTTC | TGCGAAAACG | CGGGAAAAAG | TGGAAGCGGC |
| 201 | GATGGCGGAG | CTGAATTACA | TTCCCAACCG | CGTGGCACAA | CAACTGGCGG |
| 251 | GCAAACAGTC | GTTGCTGATT | GGCGTTGCCA | CCTCCAGTCT | GGCCCTGCAC |
| 301 | GCGCCGTCGC | AAATTGTCGC | GGCGATTAAA | TCTCGCGCCG | ATCAACTGGG |
| 351 | TGCCAGCGTG | GTGGTGTCGA | TGGTAGAACG | AAGCGGCGTC | GAAGCCTGTA |
| 401 | AAGCGGCGGT | GCACAATCTT | CTCGCGCAAC | GCGTCAGTGG | GCTGATCATT |
| 451 | AACTATCCGC | TGGATGACCA | GGATGCCATT | GCTGTGGAAG | CTGCCTGCAC |
| 501 | TAATGTTCCG | GCGTTATTTC | TTGATGTCTC | TGACCAGACA | CCCATCAACA |
| 551 | GTATTATTTT | CTCCCATGAA | GACGGTACGC | GACTGGGCGT | GGAGCATCTG |
| 601 | GTCGCATTGG | GTCACCAGCA | AATGCGCCTG | TTAGCGGGCC | CATTAAGTTC |
| 651 | TGTCTCGGCG | CGTCTGCGTC | TGGCTGGCTG | GCATAAATAT | CTCACTCGCA |
| 701 | ATCAAATTCA | GCCGATAGCG | GAACGGGAAG | GCGACTGGAG | TGCCATGTCC |
| 751 | GGTTTTCAAC | AAACCATGCA | AATGCTGAAT | GAGGGCATCG | TTCCCACTGC |
| 801 | GATGCTGGTT | GCCAACGATC | AGATGGCGCT | GGGCGCAATG | CGCGCCATTA |
| 851 | CCGAGTCCGG | GCTGCGCGTT | GGTGCGGATA | TCTCGGTAGT | GGGATACGAC |
| 901 | GATACCGAAG | ACAGCTCATG | TTATATCCCG | CCGTCAACCA | CCATCAAACA |
| 951 | GGATTTTCGC | CTGCTGGGGC | AAACCAGCGT | GGACCGCTTG | CTGCAACTCT |
| 1001 | CTCAGGGCCA | GGCGGTGAAG | GGCAATCAGC | TGTTGCCCGT | CTCACTGGTG |
| 1051 | AAAAGAAAAA | CCACCCTGGC | GC'CCAATACG | CAAACCGCCT | CTCCCCGCGC |
| 1101 | GTTGGCCGAT | TCATTAATGC | AACTCGCACG | ACAGGTCTCG | AGACTGGAAA |
|  | stop codon lac I |  | start codon lac Z |  | (1) |
| 1151 | GCGGGCAGTG | AGCGCTAGGA | GGTAACTTAT | GGAA'AGCTTG | GCACTGGCCG |
| 1201 | TCGTTTTACA | ACGTCGTGAC | TGGGAAAACC | CTGGCGTTAC | CCAACTTAAT |
| 1251 | CGCCTTGCAG | CACATCCCCC | TTTCGCCAGC | TGGCGTAATA | GCGAAGAGGC |
| 1301 | CCGCACCGAT | CGCCCTTCCC | AACAGTTGCG | CAGCCTGAAT | GGCGAATGGC |
| 1351 | GCTTTGCCTG | GTTTCCGGCA | CCAGAAGCGG | TGCCGGAAAG | CTGGCTGGAG |
| 1401 | TGCGATCTTC | CTGAGGCCGA | TACTGTCGTC | GTCCCCTCAA | ACTGGCAGAT |
| 1451 | GCACGGTTAC | GATGCGCCCA | TCTACACCAA | CGTAACCTAT | CCCATTACGG |
| 1501 | TCAATCCGCC | GTTTGTTCCC | ACGGAGAATC | CGACGGGTTG | TTACTCGCTC |
| 1551 | ACATTTAATG | TTGATGAAAG | CTGGCTACAG | GAAGGCCAGA | CGCGAATTAT |
| 1601 | TTTTGATGGC | GTTAACTCGG | CGTTTCATCT | GTGGTGCAAC | GGGCGCTGGG |
| 1651 | TCGGTTACGG | CCAGGACAGT | CGTTTGCCGT | CTGAATTTGA | CCTGAGCGCA |
| 1701 | TTTTTACGCG | CCGGAGAAAA | CCGCCTCGCG | GTGATGGTGC | TGCGTTGGAG |
| 1751 | TGACGGCAGT | TATCTGGAAG | ATCAGGATAT | GTGGCGGATG | AGCGGCATTT |
| 1801 | TCCGTGACGT | CTCGTTGCTG | CATAAACCGA | CTACACAAAT | CAGCGATTTC |
| 1851 | CATGTTGCCA | CTCGCTTTAA | TGATGATTTC | AGCCGCGCTG | TACTGGAGGC |
| 1901 | TGAAGTTCAG | ATGTGCGGCG | AGTTGCGTGA | CTACCTACGG | GTAACAGTTT |
| 1951 | CTTTATGGCA | GGGTGAAACG | CAGGTCGCCA | GCGGCACCGC | GCCTTTCGGC |
| 2001 | GGTGAAATTA | TCGATGAGCG | TGGTGGTTAT | GCCGATCGCG | TCACACTACG |
| 2051 | TCTGAACGTC | GAAAACCCGA | AACTGTGGAG | CGCCGAAATC | CCGAATCTCT |
| 2101 | ATCGTGCGGT | GGTTGAACTG | CACACCGCCG | ACGGCACGCT | GATTGAAGCA |
| 2151 | GAAGCCTGCG | ATGTCGGTTT | CCGCGAGGTG | CGGATTGAAA | ATGGTCTGCT |
| 2201 | GCTGCTGAAC | GGCAAGCCGT | TGCTGATTCG | AGGCGTTAAC | CGTCACGAGC |
| 2251 | ATCATCCTCT | GCATGGTCAG | GTCATGGATG | AGCAGACGAT | GGTGCAGGAT |
| 2301 | ATCCTGCTGA | TGAAGCAGAA | CAACTTTAAC | GCCGTGCGCT | GTTCGCATTA |
| 2351 | TCCGAACCAT | CCGCTGTGGT | ACACGCTGTG | CGACCGCTAC | GGCCTGTATG |
| 2401 | TGGTGGATGA | AGCCAATATT | GAAACCCACG | GCATGGTGCC | AATGAATCGT |
| 2451 | CTGACCGATG | ATCCGCGCTG | GCTACCGGCG | ATGAGCGAAC | GCGTAACGCG |
| 2501 | AATGGTGCAG | CGCGATCGTA | ATCACCCGAG | TGTGATCATC | TGGTCGCTGG |
| 2551 | GGAATGAATC | AGGCCACGGC | GCTAATCACG | ACGCGCTGTA | TCGCTGGATC |
| 2601 | AAATCTGTCG | ATCCTTCCCG | CCCGGTGCAG | TATGAAGGCG | GCGGAGCCGA |
| 2651 | CACCACGGCC | ACCGATATTA | TTTGCCCGAT | GTACGCGCGC | GTGGATGAAG |
| 2701 | ACCAGCCCTT | CCCGGCTGTG | CCGAAATGGT | CCATCAAAAA | ATGGCTTTCG |
| 2751 | CTACCTGGAG | AGACGCGCCC | GCTGATCCTT | TGCGAATACG | CCCACGCGAT |
| 2801 | GGGTAACAGT | CTTGGCGGTT | TCGCTAAATA | CTGGCAGGCG | TTTCGTCAGT |
| 2851 | ATCCCCGTTT | ACAGGGCGGC | TTCGTCTGGG | ACTGGGTGGA | TCAGTCGCTG |
| 2901 | ATTAAATATG | ATGAAAACGG | CAACCCGTGG | TCGGCTTACG | GCGGTGATTT |
| 2951 | TGGCGATACG | CCGAACGATC | GCCAGTTCTG | TATGAACGGT | CTGGTCTTTG |
| 3001 | CCGACCGCAC | GCCGCATCCA | GCGCTGACGG | AAGCAAAACA | CCAGCAGCAG |
| 3051 | TTTTTCCAGT | TCCGTTTATC | CGGGCAAACC | ATCGAAGTGA | CCAGCGAATA |
| 3101 | CCTGTTCCGT | CATAGCGATA | ACGAGCTCCT | GCACTGGATG | GTGGCGCTGG |
| 3151 | ATGGTAAGCC | GCTGGCAAGC | GGTGAAGTGC | CTCTGGATGT | CGCTCCACAA |
| 3201 | GGTAAACAGT | TGATTGAACT | GCCTGAACTA | CCGCAGCCGG | AGAGCGCCGG |
| 3251 | GCAACTCTGG | CTCACAGTAC | GCGTAGTGCA | ACCGAACGCG | ACCGCATGGT |
| 3301 | CAGAAGCCGG | GCACATCAGC | GCCTGGCAGC | AGTGGCGTCT | GGCGGAAAAC |
| 3351 | CTCAGTGTGA | CGCTCCCCGC | CGCGTCCCAC | GCCATCCCGC | ATCTGACCAC |

TABLE 1-continued

| | | | | |
|---|---|---|---|---|
| 3401 CAGCGAAATG | GATTTTTGCA | TCGAGCTGGG | TAATAAGCGT | TGGCAATTTA |
| 3451 ACCGCCAGTC | AGGCTTTCTT | TCACAGATGT | GGATTGGCGA | TAAAAAACAA |
| 3501 CTGCTGACGC | CGCTGCGCGA | TCAGTTCACC | CGTGCACCGC | TGGATAACGA |
| 3551 CATTGGCGTA | AGTGAAGCGA | CCCGCATTGA | CCCTAACGCC | TGGGTCGAAC |
| 3601 GCTGGAAGGC | GGCGGGCCAT | TACCAGGCCG | AAGCAGCGTT | GTTGCAGTGC |
| 3651 ACGGCAGATA | CACTTGCTGA | TGCGGTGCTG | ATTACGACCG | CTCACGCGTG |
| 3701 GCAGCATCAG | GGGAAAACCT | TATTTATCAG | CCGGAAAACC | TACCGGATTG |
| 3751 ATGGTAGTGG | TCAAATGGCG | ATTACCGTTG | ATGTTGAAGT | GGCGAGCGAT |
| 3801 ACACCGCATC | CGGCGCGGAT | TGGCCTGAAC | TGCCAGCTGG | CGCAGGTAGC |
| 3851 AGAGCGGGTA | AACTGGCTCG | GATTAGGGCC | GCAAGAAAAC | TATCCCGACC |
| 3901 GCCTTACTGC | CGCCTGTTTT | GACCGCTGGG | ATCTGCCATT | GTCAGACATG |
| 3951 TATACCCCGT | ACGTCTTCCC | GAGCGAAAAC | GGTCTGCGCT | GCGGGACGCG |
| 4001 CGAATTGAAT | TATGGCCCAC | ACCAGTGCCG | CGGCGACTTC | CAGTTCAACA |
| 4051 TCAGCCGCTA | CAGTCAACAG | CAACTGATGG | AAACCAGCCA | TCGCCATCTG |
| 4101 CTGCACGCGG | AAGAAGGCAC | ATGGCTGAAT | ATCGACGGTT | TCCATATGGG |
| | | | | mutated EcoRI site[2] |
| 4151 GATTGGTGGC | GACGACTCCT | GGAGCCCGTC | AGTATCGGCG | NNNNNNCAGC |
| | | | | stop codon lac Z |
| 4201 TGAGCGCCGG | TCGCTACCAT | TACCAGTTGG | TCTGGTGTCA | AAAA<u>TAA</u>TAA |
| | | | | start codon lac Y |
| 4251 TAACCGGGCA | GGCCATGTCT | GCCCGTATTT | CGCGTAAGGA | AATCC<u>A</u>TTAT |
| 4301 <u>G</u>TACTATTTA | AAAAACACAA | ACTTTTGGAT | GTTCGGTTTA | TTCTTTTTCT |
| 4351 TTTACTTTTT | TATCATGGGA | GCCTACTTCC | CGTTTTTCCC | GATTTGGCTA |
| 4401 CATGACATCA | ACCATATCAG | CAAAAGTGAT | ACGGGTATTA | TTTTTGCCGC |
| 4451 TATTTCTCTG | TTCTCGCTAT | TATTCCAACC | GCTGTTTGGT | CTGCTTTCTG |
| 4501 ACAAACTCGG | GCTGCGCAAA | TACCTGCTGT | GGATTATTAC | CGGCATGTTA |
| 4551 GTGATGTTTG | CGCCGTTCTT | TATTTTTATC | TTCGGGCCAC | TGTTACAATA |
| 4601 CAACATTTTA | GTAGGATCGA | TTGTTGGTGG | TATTTATCTA | GGCTTTTGTT |
| 4651 TTAACGCCGG | TGCCGCAGCA | GTAGAGGCAT | TTATTGAGAA | AGTCAGCCGT |
| 4701 CGCAGTAATT | TCGAATTTGG | TCGCGCGCGG | ATGTTTGGCT | GTGTTGGCTG |
| 4751 GGCGCTGTGT | GCCTCGATTG | TCGGCATCAT | GTTCACCATC | AATAATCAGT |
| 4801 TTGTTTTCTG | GCTGGGCTCT | GGCTGTGCAC | TCATCCTCGC | CGTTTTACTC |
| 4851 TTTTTCGCCA | AAACGGATGC | GCCCTCTTCT | GCCACGGTTG | CCAATGCGGT |
| 4901 AGGTGCCAAC | CATTCGGCAT | TTAGCCTTAA | GCTGGCACTG | GAACTGTTCA |
| 4951 GACAGCCAAA | ACTGTGGTTT | TTGTCACTGT | ATGTTATTGG | CGTTTCCTGC |
| 5001 ACCTACGATG | TTTTTGACCA | ACAGTTTGCT | AATTTCTTTA | CTTCGTTCTT |
| 5051 TGCTACCGGT | GAACAGGGTA | CGCGGGTATT | TGGCTACGTA | ACGACAATGG |
| 5101 GCGAATTACT | TAACGCCTCG | ATTATGTTCT | TTGCGCCACT | GATCATTAAT |
| 5151 CGCATCGGTG | GGAAAAACGC | CCTGCTGCTG | GCTGGCACTA | TTATGTCTGT |
| 5201 ACGTATTATT | GGCTCATCGT | TCGCCACCTC | AGCGCTGGAA | GTGGTTATTC |
| 5251 TGAAAACGCT | GCATATGTTT | GAAGTACCGT | TCCTGCTGGT | GGGCTGCTTT |
| 5301 AAATATATTA | CCAGCCAGTT | TGAAGTGCGT | TTTTCAGCGA | CGATTTATCT |
| 5351 GGTCTGTTTC | TGCTTCTTTA | AGCAACTGGC | GATGATTTTT | ATGTCTGTAC |
| 5401 TGGCGGGCAA | TATGTATGAA | AGCATCGGTT | TCCAGGGCGC | TTATCTGGTG |
| 5451 CTGGGTCTGG | TGGCGCTGGG | CTTCACCTTA | ATTTCCGTGT | TCACGCTTAG |
| | | | | stop codon lac Y |
| 5501 CGGCCCCGGC | CCGCTTTCCC | TGCTGCGTCG | TCAGGTGAAT | GAAGTCGCT<u>T</u> |
| 5551 <u>A</u>AGCAATCAA | TGTCGGATGC | GGCGCGACGC | TTATCCGACC | AACATATCAT |
| | | start codon lac A | | |
| 5601 AACGGAGTGA | TCGCA<u>TTG</u>AA | CATGCCAATG | ACCGAAAGAA | TAAGAGCAGG |
| 5651 CAAGCTATTT | ACCGATATGT | GCGAAGGCTT | ACCGGAAAAA | AGACTTCGTG |
| 5701 GGAAAACGTT | AATGTATGAG | TTTAATCACT | CGCATCCATC | AGAAGTTGAA |
| 5751 AAAAGAGAAA | GCCTGATTAA | AGAAATGTTT | GCCACGGTAG | GGGAAAACGC |
| 5801 CTGGGTAGAA | CCGCCTGTCT | ATTTCTCTTA | CGGTTCCAAC | ATCCATATAG |
| 5851 GCCGCAATTT | TTATGCAAAT | TTCAATTTAA | CCATTGTCGA | TGACTACACG |
| 5901 GTAACAATCG | GTGATAACGT | ACTGATTGCA | CCCAACGTTA | CTCTTTCCGT |
| 5951 TACGGGACAC | CCTGTACACC | ATGAATTGAG | AAAAAACGGC | GAGATGTACT |
| 6001 CTTTTCCGAT | AACGATTGGC | AATAACGTCT | GGATCGGAAG | TCATGTGGTT |
| 6051 ATTAATCCAG | GCGTCACCAT | CGGGGATAAT | TCTGTTATTG | GCGCGGGTAG |
| 6101 TATCGTCACA | AAAGACATTC | CACCAAACGT | CGTGGCGGCT | GGCGTTCCTT |
| 6151 GTCGGGTTAT | TCGCGAAATA | AACGACCGGG | ATAAGCACTA | TTATTTCAAA |
| | | stop codon lac A | | |
| 6201 GATTATAAAG | TTGAATCGTC | AGTT<u>TAA</u>ATT | ATAAAATTG | CCTGATACGC |
| 6251 TGCGCTTATC | AGGCCTACAA | GTTCAGCGAT | CTACATTAGC | CGCATCCGGC |
| 6301 ATGAACAAAG | CGCAGGAACA | AGCGTCGCAT | CATGCCTCTT | TGACCCACAG |
| 6351 CTGCGGAAAA | CGTACTGGTG | CAAAACGCAG | GGTTATGATC | ATCAGCCCAA |
| 6401 CGACGCACAG | CGCATGAAAT | GCCCAGTCCA | TCAGGTAATT | GCCGCTGATA |
| 6451 CTACGCAGCA | CGCCAGAAAA | CCACGGGGCA | AGCCCGGCGA | TGATAAAACC |
| 6501 GATTCCCTGC | ATAAACGCCA | CCAGCTTGCC | AGCAATAGCC | GGTTGCACAG |
| 6551 AGTGATCGAG | CGCCAGCAGC | AAACAGAGCG | GAAACGCGCC | GCCCAGACCT |
| 6601 AACCCACACA | CCATCGCCCA | CAATACCGAC | AATTGCATCG | GCAGCCAGAT |
| 6651 AAAGCCGCAG | AACCCCACCA | GTTGTAACAC | CAGCGCCAGC | ATTAACAGTT |
| 6701 TGCGCCGATC | CTGATGGCGA | GCCATAGCAG | GCATCAGCAA | AGCTCCTGCG |
| 6751 GCTTGCCCAA | GCGTCATCAA | TGCCAGTAAG | GAACCGCTGT | ACTGCGCGCT |

TABLE 1-continued

| 6801 | GGCACCAATC | TCAATATAGA | AAGCGGGTAA | CCAGGCAATC | AGGCTGGCGT |
|------|------------|------------|------------|------------|------------|
| 6851 | AACCGCCGTT | AATCAGACCG | AAGTAAACAC | CCAGCGTCCA | CGCGCGGGGA |
| 6901 | GTGAATACCA | CGCGAACCGG | AGTGGTTGTT | GTCTTGTGGG | AAGAGGCGAC |
| 6951 | CTCGCGGGCG | CTTTGCCACC | ACCAGGCAAA | GAGCGCAACA | ACGGCAGGCA |
| 7001 | GCGCCACCAG | GCGAGTGTTT | GATACCAGGT | TTCGCTATGT | TGAACTAACC |
| 7051 | AGGGCGTTAT | GGCGGCACCA | AGCCCACCGC | CGCCCATCAG | AGCCGCGGAC |
| 7101 | CACAGCCCCA | TCACCAGTGG | CGTGCGCTGC | TGAAACCGCC | GTTTAATCAC |
| 7151 | CGAAGCATCA | CCGCCTGAAT | GATGCCGATC | CCCACCCCAC | CAAGCAGTGC |
| 7201 | GCTGCTAAGC | AGCAGCGCAC | TTTGCGGGTA | AAGCTCACGC | ATCAATGCAC |
| 7251 | CGACGGCAAT | CAGCAACAGA | CTGATGGCGA | CACTGCGACG | TTCGCTGACA |
| 7301 | TGCTGATGAA | GCCAGCTTCC | GGCCAGCGCC | AGCCCGCCCA | TGGTAACCAC |
|      |            | SalI site in pSKS107 |    |            |            |
| 7351 | CGGCAGAGCG | GTCGAC     |            |            |            |

(1) sequence in bold, between the two ' marks, is synthetic DNA used to fuse the lac operon to the lac I or lac I$^Q$ gene operon.
(2) pSKS107 contains an unsequenced mutation at the EcoR1 site normally found in the lac Z gene.

TABLE 2

Lactose Inducibility of Various Constructs

| Hours after[1] Induction | Lactose (mM) | Cells/ml | Toxin[2] (ug/ml) |
|---|---|---|---|
| MR471 | | | |
| 40 | 0 | $1.6 \times 10^{10}$ | none detected |
| 40 no lactose | 2 mM IPTG | $2.3 \times 10^{10}$ | 1003 |
| 15 | 20 | $9.1 \times 10^{9}$ | 1011 |
| 24 | 20 | $1.2 \times 10^{10}$ | 737 |
| 15 | 40 | $1.8 \times 10^{10}$ | 887 |
| 24 | 40 | $1.1 \times 10^{10}$ | 1025 |
| 23[3] | 8.3[4] | $1.9 \times 10^{10}$ | 938 |
| 39[3] | 8.3[4] | $2.0 \times 10^{10}$ | 1555 |
| MB101 containing pMYC485 | | | |
| 24 | 40 | — | 775 |
| 24 | 0 | — | none detected |
| MB101 containing pMYC1161 | | | |
| 24 | 40 | — | 300 |
| 24 | 0 | — | none detected |

[1] Cultures were induced upon reaching stationary phase.
[2] Toxin concentration was determined by laser densitometry of Coomassie-stained protein bands after electrophoresis of disrupted cells on SDS-PAGE (LKB Instructional Manual 222-010).
[3] This experiment used MR471 grown in a 10L fermentor. All other experimental data were generated using same medium in 250 ml baffled shake flasks.
[4] In the fermentor, 8.3 mM lactose/hour was fed into the culture. It was found that MR471 did not metabolize this lactose level in a fermentor, resulting in increased concentrations during the experiment. The experiments done in shake flasks were given a single dose of lactose or IPTG at the indicated times.

I claim:

1. A novel lacI ZYA operon having the sequence shown in Table 1, or mutations thereof which retain the ability to control expression of heterologous genes from lac operated promoters as does the parent operon.

2. A novel lacI$^Q$ ZYA operon having the sequence shown in Table 1, wherein base 16 is a T instead of a C as shown in the table, or mutations thereof which retain the ability to control expression of heterologous genes from lac operated promoters as does the parent operon.

3. A process for controlling the expression of a heterologous gene from a lac operated promoter which comprises culturing a microbe comprising a heterologous gene expressed from a lac operated promoter, and a lacIZYA or lacI$^Q$ZYA operon wherein the CAP binding site and lac promoter/operator is not present in the lac operon.

4. The process, according to claim 3, wherein said microbe has been transformed with a plasmid comprising the heterologous gene.

5. The process according to claim 3, wherein said microbe comprises a chromosome comprising a lacIZYA or lacI$^Q$ZYA operon wherein the CAP binding site and lac promoter/operator is not present in the lac operon.

6. A transfer vector comprising a lacIZYA or lacI$^Q$ZYA operon wherein the CAP binding site and lac promoter/operator is not present in the lac operon.

7. A microbial host transformed by the transfer vector of claim 6.

8. The transfer vector, according to claim 6, being a plasmid.

9. A process for preparing a protein product which comprises culturing a microbe comprising a heterologous gene encoding said product which is expressed from a lac promoter, and a lacIZYA or lacI$^Q$ZYA operon wherein the CAP binding site and lac promoter/operator is not present in the lac operon, until a sufficient amount of desired product is produced.

10. A process for controlling the expression of a heterologous gene from a lac operated promoter which comprises culturing a microbe comprising a heterologous gene expressed from a lac operated promoter, and a lacIZY or lacI$^Q$ZY operon wherein the CAP binding site and lac promoter/operator is not present in the lac operon.

11. The process, according to claim 10, wherein said microbe has been transformed with a plasmid comprising a heterologous gene.

12. The process according to claim 10, wherein said microbe comprises a chromosome comprising said lacIZY or lacI$^Q$ZY operon wherein the CAP binding site and lac promoter/operator is not present in the lac operon.

13. A transfer vector comprising a lacIZY or lacI$^Q$ZY operon wherein the CAP binding site and lac promoter/operator is not present in the lac operon.

14. A microbial host transformed by the transfer vector of claim 13.

15. The transfer vector, according to claim 13, being a plasmid.

16. A process for preparing a protein product which comprises culturing a microbe comprising a heterologous gene encoding said product which is expressed from a lac promoter, and a lacIZY or lacI$^Q$ZY operon wherein the CAP binding site and lac promoter/operator is not present in the lac operon, until a sufficient amount of desired product is produced.

* * * * *